(12) United States Patent
Lambert et al.

(10) Patent No.: US 10,012,587 B2
(45) Date of Patent: Jul. 3, 2018

(54) METHOD FOR CHARACTERISING A PRODUCT BY MEANS OF TOPOLOGICAL SPECTRAL ANALYSIS

(71) Applicant: TOPNIR SYSTEMS SAS, Aix en Provence (FR)

(72) Inventors: Didier Lambert, Bernos Beaulac (FR); Claude Saint Martin, Pelissane (FR); Miguel Sanchez, Lavera (FR); Bernard Ribero, Marseilles (FR)

(73) Assignee: Topnir Systems SAS, Aix en Provence (FR)

( * ) Notice: Subject to any disclaimer, the term of this patent is extended or adjusted under 35 U.S.C. 154(b) by 276 days.

(21) Appl. No.: 14/888,270

(22) PCT Filed: Apr. 25, 2014

(86) PCT No.: PCT/EP2014/058499
§ 371 (c)(1),
(2) Date: Oct. 30, 2015

(87) PCT Pub. No.: WO2014/177472
PCT Pub. Date: Nov. 6, 2014

(65) Prior Publication Data
US 2016/0061720 A1    Mar. 3, 2016

(30) Foreign Application Priority Data

Apr. 30, 2013 (EP) .................... 13290099

(51) Int. Cl.
*G06F 17/18* (2006.01)
*G01N 21/359* (2014.01)
*G01N 21/3577* (2014.01)
*G06F 11/30* (2006.01)

(52) U.S. Cl.
CPC ....... *G01N 21/359* (2013.01); *G01N 21/3577* (2013.01)

(58) Field of Classification Search
CPC .................................................... G01N 21/359
See application file for complete search history.

(56) References Cited

U.S. PATENT DOCUMENTS

| 6,897,071 B2 | 5/2005 | Sonbul |
| 2010/0211329 A1 | 8/2010 | Farquharson et al. |

FOREIGN PATENT DOCUMENTS

| EP | 0742900 | 11/1996 |
| WO | 9207326 | 4/1992 |
| WO | 2006126978 | 11/2006 |
| WO | WO 2006/126978 | * 11/2006 |

* cited by examiner

*Primary Examiner* — Phuong Huynh
(74) *Attorney, Agent, or Firm* — Gable Gotwals

(57) ABSTRACT

The invention relates to a method for generating and optimizing a bank of spectral data that can be used in a method for characterizing a target product by means of topological spectral analysis based on a limited number of available standards, the method consisting of a first step of performing the same spectral analysis on the standards, and, from the spectra obtained, forming a bank of spectral data A at multiple wavelengths and/or wavelength ranges.

14 Claims, 10 Drawing Sheets

| Absorbance Wave number (cm-1) | 4776 | 4772 | 4768 | 4764 | 4760 | 4756 | 4752 | 4748 | 4744 | 4740 | 4736 | 4732 | 4728 |
|---|---|---|---|---|---|---|---|---|---|---|---|---|---|
| Etalon | | | | | | | | | | | | | |
| A0000001 | 0.00000131 | 0.00000234 | 0.00000471 | 0.00000778 | 0.00001291 | 0.00001881 | 0.00002420 | 0.00003164 | 0.00004422 | 0.00006178 | 0.00008012 | 0.00009882 | 0.00011603 |
| A0000002 | 0.00000154 | 0.00000300 | 0.00000484 | 0.00000808 | 0.00001365 | 0.00001962 | 0.00002497 | 0.00003183 | 0.00004456 | 0.00006093 | 0.00007915 | 0.00009801 | 0.00011606 |
| A0000003 | 0.00000131 | 0.00000284 | 0.00000512 | 0.00000878 | 0.00001523 | 0.00002234 | 0.00002966 | 0.00003967 | 0.00005529 | 0.00007543 | 0.00009683 | 0.00011817 | 0.00013911 |
| A0000004 | 0.00000028 | 0.00000173 | 0.00000375 | 0.00000746 | 0.00001259 | 0.00001808 | 0.00002468 | 0.00003287 | 0.00004706 | 0.00006552 | 0.00008471 | 0.00010404 | 0.00012267 |
| A0000005 | 0.00000152 | 0.00000346 | 0.00000608 | 0.00001005 | 0.00001590 | 0.00002388 | 0.00003277 | 0.00004342 | 0.00005927 | 0.00008077 | 0.00010398 | 0.00012785 | 0.00014973 |
| A0000006 | 0.00000025 | 0.00000137 | 0.00000276 | 0.00000549 | 0.00000920 | 0.00001410 | 0.00001884 | 0.00002541 | 0.00003622 | 0.00005183 | 0.00006958 | 0.00008685 | 0.00010424 |
| A0000007 | 0.00000115 | 0.00000192 | 0.00000381 | 0.00000714 | 0.00001208 | 0.00001862 | 0.00002413 | 0.00003267 | 0.00004633 | 0.00006518 | 0.00008486 | 0.00010414 | 0.00012311 |
| A0000008 | 0.00000145 | 0.00000286 | 0.00000597 | 0.00001025 | 0.00001641 | 0.00002401 | 0.00003255 | 0.00004393 | 0.00006125 | 0.00008424 | 0.00010897 | 0.00013581 | 0.00016053 |
| A0000009 | 0.00000196 | 0.00000443 | 0.00000613 | 0.00000825 | 0.00001145 | 0.00001403 | 0.00001617 | 0.00001990 | 0.00002562 | 0.00003560 | 0.00004941 | 0.00006621 | 0.00008322 |

| Absorbance Wave number (cm-1) | 4352 | 4348 | 4344 | 4340 | 4336 | 4332 | 4328 | 4324 | 4320 | 4316 | 4312 | 4308 | 4304 |
|---|---|---|---|---|---|---|---|---|---|---|---|---|---|
| Etalon | | | | | | | | | | | | | |
| A0000001 | 0.00966521 | 0.01052209 | 0.01158039 | 0.01273609 | 0.01366893 | 0.01401955 | 0.01384877 | 0.01353086 | 0.01333914 | 0.01318977 | 0.01295103 | 0.01250628 | 0.01190033 |
| A0000002 | 0.00962570 | 0.01045172 | 0.01147713 | 0.01259841 | 0.01351549 | 0.01386926 | 0.01370155 | 0.01337238 | 0.01316494 | 0.01301322 | 0.01279028 | 0.01237890 | 0.01181515 |
| A0000003 | 0.00971714 | 0.01051752 | 0.01151046 | 0.01260728 | 0.01350349 | 0.01385874 | 0.01371417 | 0.01342094 | 0.01323014 | 0.01306308 | 0.01280913 | 0.01238076 | 0.01181617 |
| A0000004 | 0.00970203 | 0.01053299 | 0.01156151 | 0.01269044 | 0.01360349 | 0.01396508 | 0.01381938 | 0.01353130 | 0.01333327 | 0.01313686 | 0.01284140 | 0.01236973 | 0.01178167 |
| A0000005 | 0.00983396 | 0.01059963 | 0.01155613 | 0.01260533 | 0.01346771 | 0.01381668 | 0.01367895 | 0.01339166 | 0.01320615 | 0.01304760 | 0.01281606 | 0.01240677 | 0.01184798 |
| A0000006 | 0.00975312 | 0.01059458 | 0.01165282 | 0.01283536 | 0.01379368 | 0.01414591 | 0.01392945 | 0.01352795 | 0.01325576 | 0.01296382 | 0.01265066 | 0.01220577 | 0.01166779 |
| A0000007 | 0.00971298 | 0.01053791 | 0.01157010 | 0.01271768 | 0.01364754 | 0.01400085 | 0.01381945 | 0.01347245 | 0.01322868 | 0.01300856 | 0.01271797 | 0.01227517 | 0.01172447 |
| A0000008 | 0.00973713 | 0.01055416 | 0.01158105 | 0.01271146 | 0.01362481 | 0.01395885 | 0.01376642 | 0.01341727 | 0.01316979 | 0.01298435 | 0.01274264 | 0.01233134 | 0.01177974 |
| A0000009 | 0.00973863 | 0.01054689 | 0.01155098 | 0.01265425 | 0.01355805 | 0.01391147 | 0.01373056 | 0.01336471 | 0.01310149 | 0.01290984 | 0.01267387 | 0.01227335 | 0.01172989 |

SPECTRAL DATABASE A

FIGURE 2

| Wave number VGS | W1 | W2 | W3 | W4 | W5 | W6 | W7 | W8 | W9 |
|---|---|---|---|---|---|---|---|---|---|
| | 1.52455E-07 | 5.98E-06 | 5.43E-06 | 9.39E-06 | 1.38E-05 | 2.07E-05 | 2.62E-05 | 3.04E-05 | 4.14E-05 |
| | 1.12042E-07 | 6.81E-06 | 5.33E-06 | 9.54E-06 | 1.46E-05 | 2.15E-05 | 2.69E-05 | 3.11E-05 | 4.18E-05 |
| | 1.55755E-06 | 4.53E-06 | 6.07E-06 | 9.07E-06 | 1.45E-05 | 2.07E-05 | 2.6E-05 | 3.13E-05 | 4.12E-05 |
| | 4.15098E-08 | 6.65E-06 | 5.33E-06 | 9.63E-06 | 1.45E-05 | 2.09E-05 | 2.62E-05 | 3.12E-05 | 4.14E-05 |
| | 1.28445E-07 | 6.52E-06 | 5.19E-06 | 9.68E-06 | 1.46E-05 | 2.21E-05 | 2.7E-05 | 3.08E-05 | 4.2E-05 |
| | 1.52686E-06 | 4.24E-06 | 6.16E-06 | 8.66E-06 | 1.36E-05 | 1.97E-05 | 2.57E-05 | 3.07E-05 | 4.05E-05 |
| | 1.45709E-06 | 4.02E-06 | 6.06E-06 | 9.18E-06 | 1.47E-05 | 2.04E-05 | 2.63E-05 | 3.14E-05 | 4.1E-05 |
| | 1.8449E-06 | 4.52E-06 | 5.79E-06 | 8.99E-06 | 1.43E-05 | 2.02E-05 | 2.62E-05 | 3.16E-05 | 4.17E-05 |
| | 1.73044E-06 | 4.4E-06 | 6.12E-06 | 8.94E-06 | 1.42E-05 | 2.04E-05 | 2.63E-05 | 3.11E-05 | 4.07E-05 |
| | 1.11909E-06 | 3.85E-06 | 6.37E-06 | 9.31E-06 | 1.43E-05 | 2.08E-05 | 2.59E-05 | 3.07E-05 | 4.07E-05 |
| VGS | 9.67038E-07 | 5.15E-06 | 5.79E-06 | 9.24E-06 | 1.43E-05 | 2.07E-05 | 2.63E-05 | 3.11E-05 | 4.12E-05 |
| σ | 7.6254E-07 | 1.19E-06 | 4.27E-07 | 3.31E-07 | 3.79E-07 | 6.75E-07 | 4.21E-07 | 3.79E-07 | 4.99E-07 |
| $\frac{m}{\sigma}*100$ | 78.85 | 23.09 | 7.38 | 3.58 | 2.65 | 3.26 | 1.60 | 1.22 | 1.21 |

SPECTRAL DATABASE B

FIGURE 3

| Absorbance | Wave number(cm-1) | 4776 | 4772 | 4768 | 4764 | 4760 | 4756 | 4752 | 4748 | 4744 | 4740 | 4736 | 4732 | 4728 |
|---|---|---|---|---|---|---|---|---|---|---|---|---|---|---|
| Etalon | | | | | | | | | | | | | | |
| A000001 | | 0.00000131 | 0.00000234 | 0.00000471 | 0.00000778 | 0.00001291 | 0.00001881 | 0.00002420 | 0.00003164 | 0.00004422 | 0.00006178 | 0.00008012 | 0.00009882 | 0.00011603 |
| A000002 | | 0.00000154 | 0.00000309 | 0.00000484 | 0.00000808 | 0.00001365 | 0.00001962 | 0.00002497 | 0.00003183 | 0.00004456 | 0.00006093 | 0.00007915 | 0.00009801 | 0.00011606 |
| A000003 | | 0.00000131 | 0.00000284 | 0.00000512 | 0.00000878 | 0.00001523 | 0.00002234 | 0.00002966 | 0.00003987 | 0.00005529 | 0.00007543 | 0.00009683 | 0.00011817 | 0.00013911 |
| A000004 | | 0.00000138 | 0.00000173 | 0.00000375 | 0.00000746 | 0.00001259 | 0.00001808 | 0.00002468 | 0.00003287 | 0.00004706 | 0.00006552 | 0.00008471 | 0.00010404 | 0.00012267 |
| A000005 | | 0.00000152 | 0.00000346 | 0.00000608 | 0.00001005 | 0.00001590 | 0.00002388 | 0.00003277 | 0.00004342 | 0.00005927 | 0.00008077 | 0.00010398 | 0.00012785 | 0.00014973 |
| A000006 | | 0.00000025 | 0.00000137 | 0.00000376 | 0.00000549 | 0.00000920 | 0.00001410 | 0.00001884 | 0.00002541 | 0.00003622 | 0.00005183 | 0.00006968 | 0.00008585 | 0.00010424 |
| A000007 | | 0.00000115 | 0.00000192 | 0.00000381 | 0.00000714 | 0.00001208 | 0.00001862 | 0.00002413 | 0.00003267 | 0.00004633 | 0.00006518 | 0.00008486 | 0.00010414 | 0.00012311 |
| A000008 | | 0.00000145 | 0.00000286 | 0.00000597 | 0.00001025 | 0.00001641 | 0.00002401 | 0.00003255 | 0.00004393 | 0.00006125 | 0.00008424 | 0.00010897 | 0.00013581 | 0.00016053 |
| A000009 | | 0.00000196 | 0.00000443 | 0.00000613 | 0.00000825 | 0.00001145 | 0.00001403 | 0.00001617 | 0.00001990 | 0.00002562 | 0.00003560 | 0.00004941 | 0.00006621 | 0.00008322 |

IMPROVED SPECTRAL DATABASE A'

FIGURE 4

| Absorbance Name | wt% | Germ 1 | Germ 2 | Germ 3 | 4764 | 4760 | 4756 | 4752 | 4748 | 4744 | 4740 | 4736 |
|---|---|---|---|---|---|---|---|---|---|---|---|---|
| A0000001 | | | | | 7.78E-06 | 1.29E-05 | 1.88E-05 | 2.42E-05 | 3.16E-05 | 4.42E-05 | 6.18E-05 | 8.01E-05 |
| A0000002 | | | | | 8.08E-06 | 1.37E-05 | 1.96E-05 | 2.5E-05 | 3.18E-05 | 4.46E-05 | 6.09E-05 | 7.91E-05 |
| A0000003 | | | | | 8.78E-06 | 1.52E-05 | 2.23E-05 | 2.97E-05 | 3.99E-05 | 5.53E-05 | 7.54E-05 | 9.68E-05 |
| A0000004 | | | | | 7.46E-06 | 1.26E-05 | 1.81E-05 | 2.47E-05 | 3.29E-05 | 4.71E-05 | 6.55E-05 | 8.47E-05 |
| A0000005 | | | | | 1.01E-05 | 1.59E-05 | 2.39E-05 | 3.28E-05 | 4.34E-05 | 5.93E-05 | 8.06E-05 | 0.000104 |
| A0000006 | | | | | 5.49E-06 | 9.2E-06 | 1.41E-05 | 1.88E-05 | 2.54E-05 | 3.62E-05 | 5.18E-05 | 6.97E-05 |
| A0000007 | | | | | 7.14E-06 | 1.21E-05 | 1.85E-05 | 2.41E-05 | 3.27E-05 | 4.63E-05 | 6.52E-05 | 8.49E-05 |
| A0000008 | | | | | 1.03E-05 | 1.64E-05 | 2.4E-05 | 3.26E-05 | 4.39E-05 | 6.13E-05 | 8.42E-05 | 0.000109 |
| A0000009 | | | | | 6.25E-06 | 1.15E-05 | 1.4E-05 | 1.62E-05 | 1.99E-05 | 2.56E-05 | 3.56E-05 | 4.94E-05 |
| 12G022 | 0.564 | A0000003 | A0000006 | | 7.35E-06 | 1.26E-05 | 1.88E-05 | 2.49E-05 | 3.35E-05 | 4.7E-05 | 6.51E-05 | 8.5E-05 |
| | 0.436 | | | | | | | | | | | |
| 12G011 | 0.654 | A0000009 | A0000001 | | 8.09E-06 | 1.2E-05 | 1.57E-05 | 1.9E-05 | 2.4E-05 | 3.21E-05 | 4.47E-05 | 6E-05 |
| | 0.346 | | | | | | | | | | | |
| 12G036 | 0.44 | A0000008 | A0000004 | | 8.69E-06 | 1.43E-05 | 2.07E-05 | 2.81E-05 | 3.77E-05 | 5.33E-05 | 7.38E-05 | 9.54E-05 |
| | 0.55 | | | | | | | | | | | |
| 13G038 | 0.747 | A0000008 | A0000002 | A0000004 | 9.71E-06 | 1.57E-05 | 2.29E-05 | 3.06E-05 | 4.09E-05 | 5.7E-05 | 7.83E-05 | 0.000101 |
| | 0.258 | | | | | | | | | | | |
| | -0.005 | | | | | | | | | | | |
| 13G025 | 0.5825 | A0000008 | A0000005 | A0000003 | 1E-05 | 1.61E-05 | 2.38E-05 | 3.23E-05 | 4.33E-05 | 6E-05 | 8.22E-05 | 0.000106 |
| | 0.3020 | | | | | | | | | | | |
| | 0.1155 | | | | | | | | | | | |
| 13G019 | 0.094 | A0000004 | A0000005 | A0000007 | 7.43E-06 | 1.25E-05 | 1.81E-05 | 2.46E-05 | 3.28E-05 | 4.7E-05 | 6.54E-05 | 8.46E-05 |
| | -0.00047 | | | | | | | | | | | |
| | 0.00647 | | | | | | | | | | | |

ENLARGED SPECTRAL DATABASE E

FIGURE 5

| Absorbance Name | wt. | Germ | wt.% | 4764 | 4760 | 4756 | 4752 | 4748 | 4744 | 4740 | 4736 | 4732 |
|---|---|---|---|---|---|---|---|---|---|---|---|---|
| A0000001 | | | | 7.78E-06 | 1.29E-05 | 1.88E-05 | 2.42E-05 | 3.16E-05 | 4.42E-05 | 6.18E-05 | 8.01E-05 | 9.88E-05 |
| A0000002 | | | | 8.08E-06 | 1.37E-05 | 1.96E-05 | 2.5E-05 | 3.18E-05 | 4.46E-05 | 6.09E-05 | 7.91E-05 | 9.8E-05 |
| A0000003 | | | | 8.78E-06 | 1.52E-05 | 2.23E-05 | 2.97E-05 | 3.99E-05 | 5.53E-05 | 7.54E-05 | 9.68E-05 | 0.000118 |
| A0000004 | | | | 7.46E-06 | 1.26E-05 | 1.81E-05 | 2.47E-05 | 3.29E-05 | 4.71E-05 | 6.55E-05 | 8.47E-05 | 0.000104 |
| A0000005 | | | | 1.01E-05 | 1.59E-05 | 2.39E-05 | 3.28E-05 | 4.34E-05 | 5.93E-05 | 8.08E-05 | 0.000104 | 0.000128 |
| A0000006 | | | | 5.49E-06 | 9.2E-06 | 1.41E-05 | 1.88E-05 | 2.54E-05 | 3.62E-05 | 5.18E-05 | 6.97E-05 | 8.68E-05 |
| A0000007 | | | | 7.14E-06 | 1.21E-05 | 1.86E-05 | 2.41E-05 | 3.27E-05 | 4.63E-05 | 6.52E-05 | 8.49E-05 | 0.000104 |
| A0000008 | | | | 1.03E-05 | 1.64E-05 | 2.4E-05 | 3.26E-05 | 4.39E-05 | 6.13E-05 | 8.42E-05 | 0.000109 | 0.000136 |
| A0000009 | | | | 8.25E-06 | 1.15E-05 | 1.4E-05 | 1.62E-05 | 1.99E-05 | 2.56E-05 | 3.56E-05 | 4.94E-05 | 6.62E-05 |
| MEG001 | PAL054 | A0000009 | 0.15 | 4.45E-06 | 7.13E-06 | 9.35E-06 | 1.12E-05 | 1.44E-05 | 1.95E-05 | 2.84E-05 | 4.08E-05 | 5.62E-05 |
| MEG002 | PAL014 | A0000005 | -0.05 | 1.15E-05 | 1.78E-05 | 2.63E-05 | 3.57E-05 | 4.69E-05 | 6.36E-05 | 8.61E-05 | 0.00011 | 0.000135 |
| MEG003 | PAL035 | A0000008 | 0.08 | 8.11E-06 | 1.37E-05 | 2.06E-05 | 2.84E-05 | 3.88E-05 | 5.48E-05 | 7.6E-05 | 9.89E-05 | 0.000124 |
| MEG004 | PRF006 | A0000002 | 0.021655 | 8.65E-06 | 1.43E-05 | 2.03E-05 | 2.57E-05 | 3.26E-05 | 4.53E-05 | 6.16E-05 | 7.98E-05 | 9.88E-05 |
| MEG005 | PRF004 | A0000007 | -0.07268 | 4.86E-06 | 9.48E-06 | 1.56E-05 | 2.07E-05 | 2.94E-05 | 4.35E-05 | 6.29E-05 | 8.26E-05 | 0.000102 |
| MEG006 | PRF074 | A0000003 | 0.028752 | 9.54E-06 | 1.61E-05 | 2.33E-05 | 3.07E-05 | 4.07E-05 | 5.59E-05 | 7.58E-05 | 9.72E-05 | 0.000119 |

ENLARGED SPECTRAL DATABASE EE

FIGURE 6

| Absorbance | Germ 1 | Germ 2 | Germ 3 | wt. | wt.% | 4764 | 4760 | 4756 | 4752 | 4748 | 4744 | 4740 |
|---|---|---|---|---|---|---|---|---|---|---|---|---|
| Name | | | | | | | | | | | | |
| A0000001 | | | | | | 7.78E-06 | 1.29E-05 | 1.88E-05 | 2.42E-05 | 3.16E-05 | 4.42E-05 | 6.18E-05 |
| A0000002 | | | | | | 8.08E-06 | 1.37E-05 | 1.96E-05 | 2.5E-05 | 3.18E-05 | 4.46E-05 | 6.09E-05 |
| A0000003 | | | | | | 8.78E-06 | 1.52E-05 | 2.23E-05 | 2.97E-05 | 3.99E-05 | 5.53E-05 | 7.54E-05 |
| A0000004 | | | | | | 7.46E-06 | 1.26E-05 | 1.81E-05 | 2.47E-05 | 3.29E-05 | 4.71E-05 | 6.55E-05 |
| A0000005 | | | | | | 1.01E-05 | 1.59E-05 | 2.39E-05 | 3.28E-05 | 4.34E-05 | 5.93E-05 | 8.08E-05 |
| A0000006 | | | | | | 5.49E-06 | 9.2E-06 | 1.41E-05 | 1.88E-05 | 2.54E-05 | 3.62E-05 | 5.18E-05 |
| A0000007 | | | | | | 7.14E-06 | 1.21E-05 | 1.86E-05 | 2.41E-05 | 3.27E-05 | 4.63E-05 | 6.52E-05 |
| A0000008 | | | | | | 1.03E-05 | 1.64E-05 | 2.4E-05 | 3.26E-05 | 4.39E-05 | 6.13E-05 | 8.42E-05 |
| A0000009 | | | | | | 8.25E-06 | 1.15E-05 | 1.4E-05 | 1.62E-05 | 1.99E-05 | 2.56E-05 | 3.56E-05 |
| MEP001 | A0000002 | A0000006 | 0 | PAL031 | 0.56 / 0.34 / 0.1 0.304 / 0.646 / | 4.86E-06 | 8.85E-06 | 1.35E-05 | 1.8E-05 | 2.41E-05 | 3.54E-05 | 5.04E-05 |
| MEP002 | A0000005 | A0000003 | 0 | PRF028 | 0.05 1.1726 / -0.0926 | 1.05E-05 | 1.68E-05 | 2.45E-05 | 3.24E-05 | 4.26E-05 | 5.78E-05 | 7.8E-05 |
| MEP003 | A0000005 | A0000008 | 0 | PRF063 | / -0.08 0.306 / -0.0530 / | 8.68E-06 | 1.44E-05 | 2.21E-05 | 3.1E-05 | 4.19E-05 | 5.78E-05 | 7.97E-05 |
| MEP004 | A0000006 | A0000009 | A0000002 | PAL037 | 0.647 / 0.1 0.6062 / 0.314 / | 4.89E-06 | 9.38E-06 | 1.46E-05 | 1.93E-05 | 2.55E-05 | 3.67E-05 | 5.17E-05 |
| MEP005 | A0000008 | A0000005 | A0000003 | PAL006 | 0.1198 / -0.04 0.273 / 0.4170 / | 1.11E-05 | 1.76E-05 | 2.56E-05 | 3.44E-05 | 4.59E-05 | 6.33E-05 | 8.63E-05 |
| MEP006 | A0000002 | A0000006 | A0000005 | PRF025 | 0.22 / 0.09 | 9.96E-06 | 1.52E-05 | 2.16E-05 | 2.8E-05 | 3.54E-05 | 4.75E-05 | 6.44E-05 |

ENLARGED SPECTRAL DATABASE EEI

FIGURE 7

| Name | Kcy | Ksatu | Karo | Kiso | Kene | xxxx |
|---|---|---|---|---|---|---|
| CRK0071 | 124.2982 | 30.2213 | 6.1022 | 20.4044 | 22.6714 | |
| CRK0075 | 123.6416 | 30.3821 | 6.0959 | 20.0519 | 22.6293 | |
| CRK0098 | 123.3631 | 29.719 | 6.1168 | 21.0968 | 22.9267 | |
| CRK0102 | 122.6272 | 29.1777 | 6.1166 | 20.8441 | 23.3606 | |
| CRK0116 | 120.3105 | 29.5099 | 6.1134 | 21.0583 | 23.0629 | |
| HVY0068 | 144.4259 | 52.0212 | 5.9475 | 22.2027 | 13.5996 | |
| HVY0088 | 141.8204 | 47.8997 | 6.0091 | 23.0564 | 14.2034 | |
| HVY0093 | 143.0184 | 49.2953 | 5.9834 | 22.8627 | 14.0157 | |
| HVY0100 | 142.1157 | 48.486 | 5.9932 | 22.8486 | 14.183 | |
| HVY0106 | 143.3684 | 50.5179 | 5.9642 | 22.8179 | 13.8181 | |
| KER0072 | 114.2108 | 61.7041 | 5.8061 | 22.7724 | 13.9045 | |
| KER0076 | 112.7754 | 59.6154 | 5.8289 | 23.7607 | 14.191 | |
| KER0079 | 113.9782 | 56.389 | 5.8904 | 22.7878 | 14.299 | |
| KER0080 | 113.2538 | 57.5513 | 5.8681 | 23.0583 | 14.2554 | |
| KER0082 | 114.2399 | 62.3519 | 5.8108 | 23.6506 | 13.8976 | |
| LGT0067 | 130.8834 | 53.1217 | 5.9227 | 22.969 | 13.9002 | |
| LGT0087 | 129.4485 | 49.2411 | 5.9723 | 23.7952 | 14.4472 | |
| LGT0096 | 129.5462 | 48.6752 | 5.9809 | 23.382 | 14.5025 | |
| LGT0099 | 129.1717 | 48.8969 | 5.9775 | 23.6349 | 14.5186 | |
| LGT0105 | 129.4355 | 50.1752 | 5.9592 | 23.4217 | 14.267 | |

Table of aggregates

ENLARGED SPECTRAL DATABASE E – with characterization

METHOD FOR CHARACTERISING A PRODUCT BY MEANS OF TOPOLOGICAL SPECTRAL ANALYSIS

CROSS-REFERENCE TO RELATED APPLICATIONS

This application is the United States National Phase of Patent Application No. PCT/EP2014/058499 filed 25 Apr. 2014, which claims priority to European Patent Application No. 13290099.4 filed 30 Apr. 2013, each of which is incorporated herein by reference.

The present invention concerns a method of characterization of a product by topological spectral analysis.

The present invention also concerns the formation of an enlarged spectral database to be used in the improved characterization of a product by topological spectral analysis.

More particularly, the present invention concerns a method of characterization of a product by topological spectral analysis in the near infrared ("NIR").

The present invention also concerns a device for characterization of such a product by topological spectral analysis.

In particular, the present invention concerns the formation of an enlarged spectral database able to be used for the improved characterization of a product by topological spectral analysis.

The characterization of a product according to the present invention may consist in a determination and/or a prediction of any chemical, physical or physico-chemical characteristic of said product and/or the identification of a type and/or family of products.

Patent EP0742900 of the applicant constitutes the reference for the field of topological spectral analysis. It describes a method of determination or prediction of a value Px, a property of a substance X or a property of a product resulting from a process coming from said substance or the yield of said process, which method consists in measuring the absorption $D_i x$ of said substance at more than one wavelength in the region of 600 to 2600 nm, comparing the indicator signals of these absorptions or their mathematical functions with indicator signals of absorptions Dim at the same wavelengths or their mathematical functions for a certain number of standards S in a database for which one knows said property or yield P, and selecting in the database at least one and preferably at least 2 standards Sm having the smallest mean values for the absolute values of the difference at each wavelength i between the signal for the substance and the signal for the standard Sm in order to obtain the value Px, and taking the mean of said properties or yields Pm, when more than one standard Sm is selected.

Although the application of techniques of mathematical analysis to spectral data has been described in patent EP0742900, U.S. Pat. No. 6,897,071 also described the integration of the use of NIR topological analysis and the techniques of the partial least squares within a single chemometric approach. In particular, U.S. Pat. No. 6,897,071 claims a method for analysis of a substance having an absorption in the NIR region, comprising: a step of data collection by the acquisition of a first set of data coming from NIR spectroscopic data of samples by subjecting the substance to a NIR spectroscopy; a step of data generation by the generating of a second set of data coming from NIR spectroscopic data by subjecting the first set of data to a partial least squares regression technique; and an identification step by the identification of a compound of the substance by means of a NIR topological analysis of this second data set.

Topological spectral analysis has many advantages compared to the classical mathematical regression methods. The numerical methods described for the modeling of the physicochemical properties of substances based on spectral analysis are of a correlation type and involve relations of a regression kind between the property (or properties) being studied. Among such multiple variable analysis one finds multilinear regression (MLR), principal component regression (PLR), canonical regression and partial least squares (PLS) regression. In all instances, one looks for a relation between the property and the spectrum which can be linear but is usually quadratic or a higher algebraic form containing regression coefficients applied to each absorption. Moreover, the establishing of any regression requires a progressive calibration, since the approach is empirical and not supported by any theory.

Thus, WO-A-9207326 describes a method of estimation of property and/or composition data of a test sample, consisting in performing a spectral measurement on the test sample and estimating the property and/or composition data of the test sample from its measured spectrum, based on a predictive model correlating the spectra of the calibration sample with the property and/or composition data of said calibration samples, in which one performs a determination, based on a checking of the measured spectrum against the predictive model to find out whether the measured spectrum is within the range of the calibration sample spectra in the model, and a response is generated if the result of the check is negative, this response consisting in particular in isolating the test sample, analyzing it with the help of a separate method to determine its property and/or composition data, and updating the predictive model with this data and with the spectral measurement data obtained.

These techniques have drawbacks, chief of which is the need to establish a strong correlation between the spectrum and the property, and their difficulty in handling the positive or negative synergy between the components contributing to this property. For example, to determine the chemical composition of LINA (linear, isoparaffinic, naphthenic, aromatic) in a hydrocarbon feedstock for a catalytic reformer, the use of a PLS technique based on NIR spectra has been described. The model works well on the calibration set but the response of the models when one adds pure hydrocarbons, such as cyclohexane, is not satisfactory, since the model predicts variations in content of isoparaffins and naphthenes which are the opposite of those experimentally found. What is more, there are other practical difficulties, primarily due to the need to identify samples of families having the same type of relation between the spectra and the properties being modeled. Thus, the model may be limited, in particular with a nonlinear relation between the spectrum and the property. The precision of the model is reduced especially when at the limits of the available data. The stability of the model is also a problem, as is the need to perform laborious revisions when adding new standards to obtain the new model, in particular when adjusting to a new feedstock for a process; thus, the checking of 6 properties for 4 products emerging from a distillation unit requires 24 models, each of which needs to be modified for each modification of the feedstock not included in the calibration. Another major drawback found with these techniques occurs when a point being analyzed is situated outside the previously established model; it is then necessary to generate a new database and a new model for each property, which makes this type of technique not only little responsive, but also requiring many more hours of work time.

As for US2010/0211329, this describes a method and a device for the determination of the class, the grade and the properties of hydrocarbon samples—regardless of the ambient temperature, the temperature of the instrumentation and/or that of the sample—by means of mathematical correlations between the class, the grade and the properties of the hydrocarbons and their spectra—in particular their Raman spectra—from a database populated with samples and their measured properties and their spectra. In particular, US2010/0211329 claims the combined use of rough mathematical models with more refined mathematical models.

It should be noted that topological spectral analysis as such has not really evolved since the applicant's patent EP0742900. Thus, the present invention involves an improvement of said method of topological spectral analysis. The characteristics of this new method of topological spectral analysis as well as its advantages will be described in detail in the following specification, as well as the examples, figures and claims. Other goals and advantages of the present invention will appear in the course of the following specification, making reference to sample embodiments given only as illustration and not as a limitation.

The understanding of this specification will be facilitated by regarding the enclosed FIGS. 1 to 10 in which:

FIG. 2 shows a spectral database example A,

Figure 8:
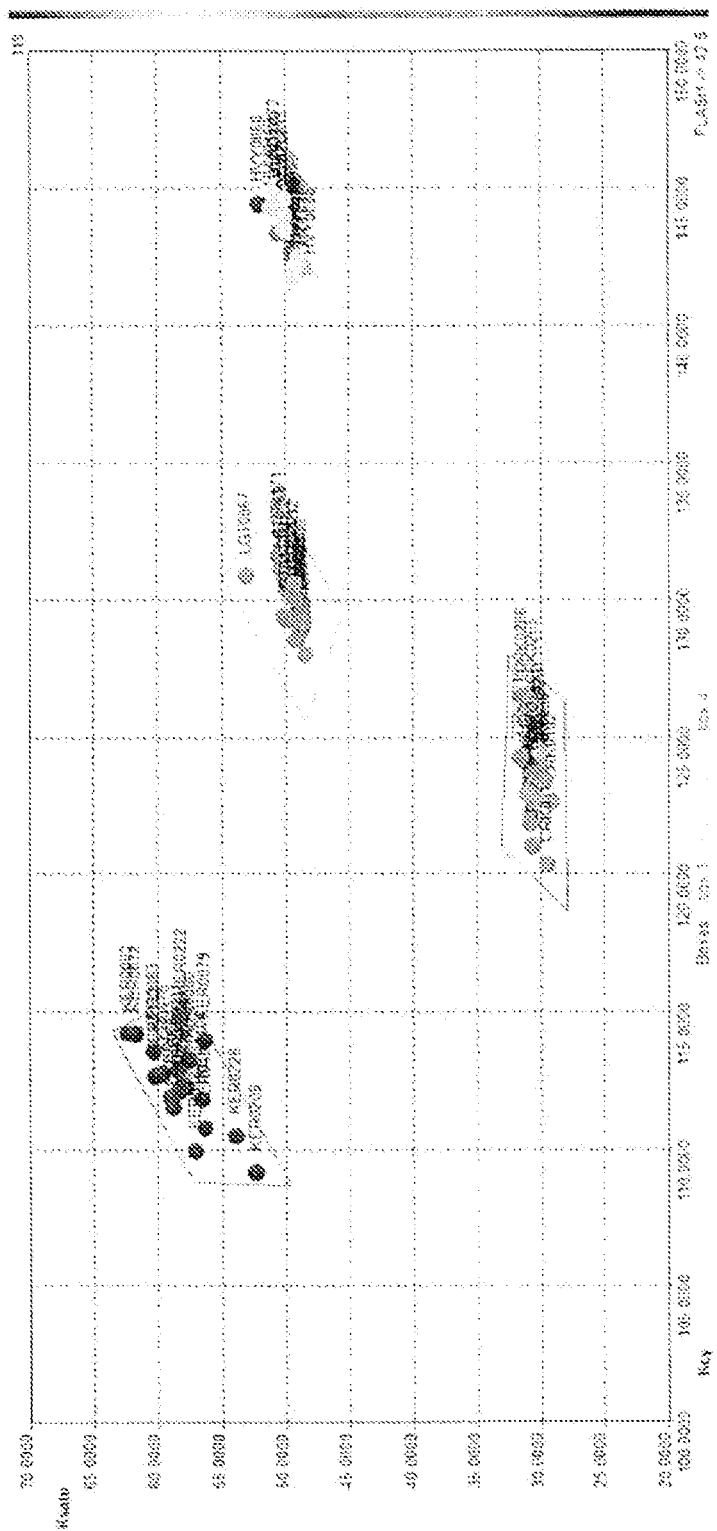
Figure 10:
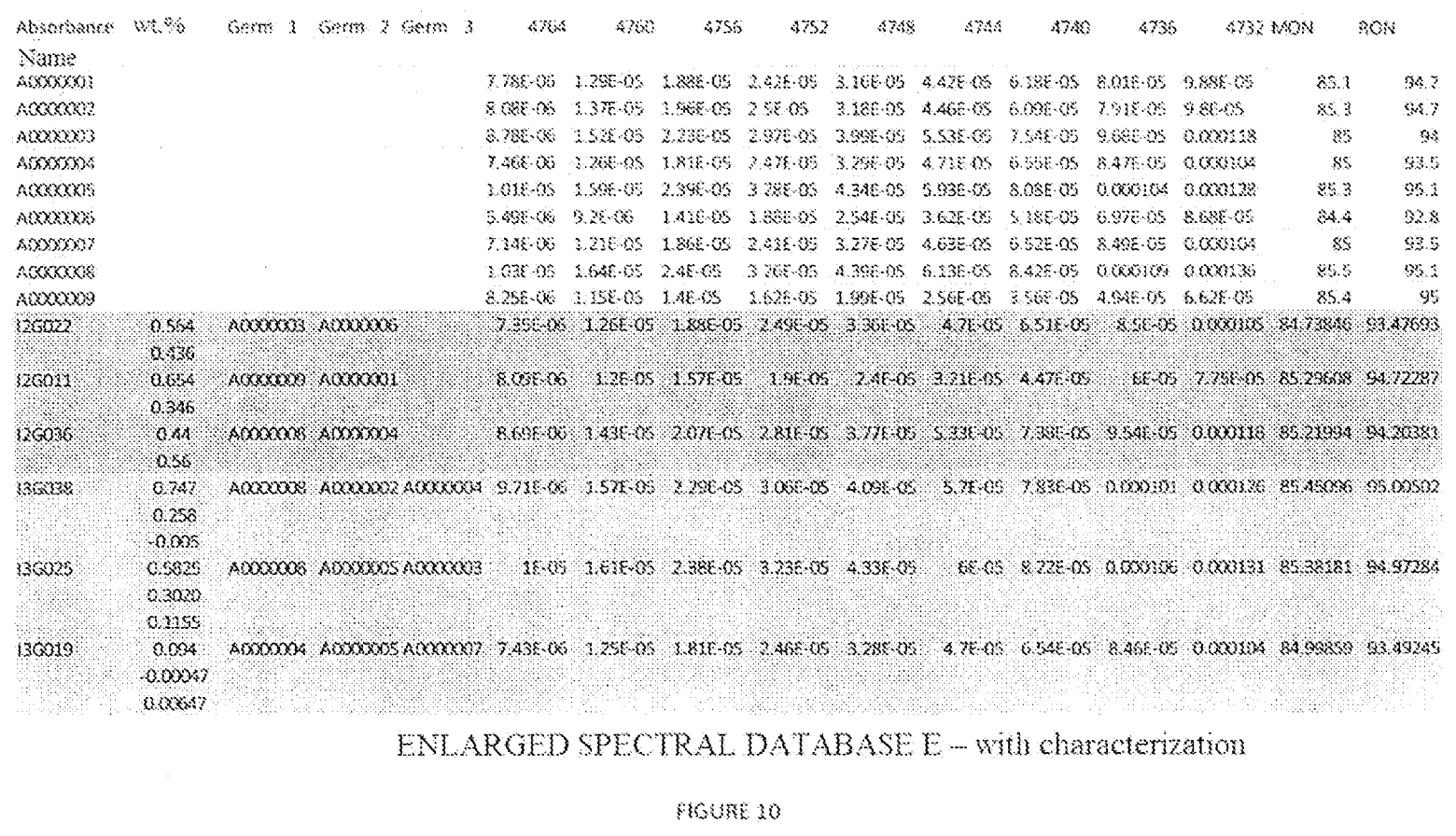

FIG. 3 shows a spectral database example B (detection of polluting wavelengths), FIG. 4 shows an improved spectral database example A' (spectral database A in which the spectral data corresponding to the polluting wavelengths have been eliminated), FIG. 5 shows an enlarged spectral database example E (spectral database A or A' in which intergerms have been added), FIG. 6 shows an enlarged spectral database example EE (spectral database A and/or E in which extragerms have been added), FIG. 7 shows an enlarged spectral database example EEI (spectral database E and/or EE in which extragerms' have been added), FIGS. 8 and 9 show, respectively, a graph and a table representing discriminant aggregates, and FIG. 10 shows a spectral database of the type of FIG. 5 in which the measured characterizations of the standards and calculations of the intergerms have been added.

In particular, all the chemometric approaches of spectral analysis of the prior art require the establishing of a spectral database made up from a very large initial number of samples and/or standards. Although the prior art cites spectral database formations based on at least 60 or at least 100 samples and/or standards, all the examples describe databases made up of a distinctly larger number of samples. This number is even larger in the chemometric approaches using the mathematical regression methods, whose databases are made up of hundreds or even thousands of samples and/or standards. The present invention is able to overcome this prior requirement, which opens up a considerable number of new applications as shown below.

Thus, first of all, the method according to the present invention consists in the preparation of an enlarged spectral database E for a limited number of materials with available standards.

The present invention can be applied advantageously to all type of spectroscopy, such as but not limited to Raman spectroscopy, RMN, the infrared range, the UV-visible range, or the near infrared (NIR) range. Preferably, the present invention will be applied to NIR spectroscopy. In fact, NIR spectroscopy presents many advantages as compared to other analysis methods, for example, at refineries, petrochemical or chemical locations, as well as all the fields where the characterization of chemical products [is done], such as hydrocarbons, and especially fuels, and it can handle a large number of repetitive applications with precision, speed, and an in-line process. Moreover, the NIR region between 800 and 2500 nm contains all of the molecular information in the form of combinations and harmonics of polyatomic vibrations.

In a first step, one performs a selected type of spectral analysis on each of the standards and begins to populate the spectral database A by registering there the spectra (for example, in numerical or digitized form), preferably the NIR spectra, at several wavelengths (or wave numbers) for a limited number of materials of available standards.

Figure 1:
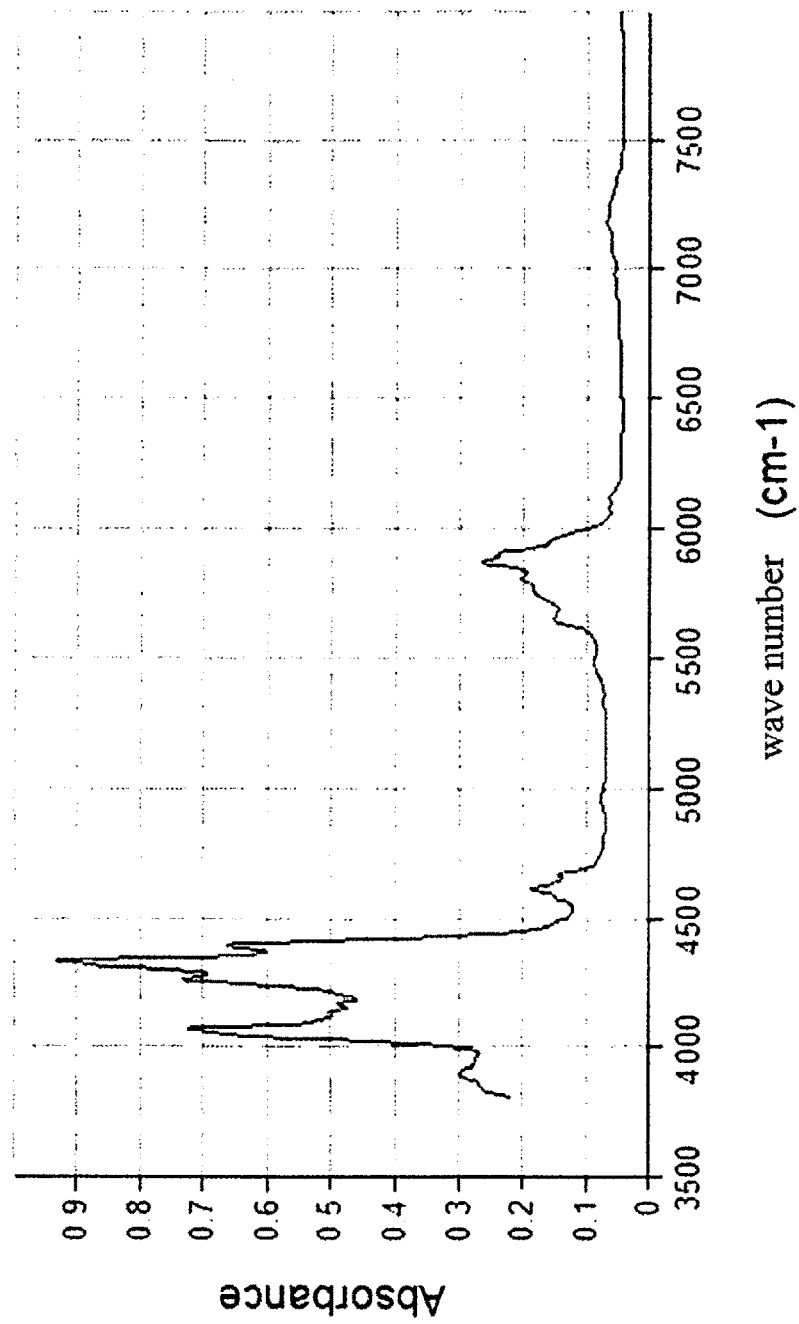
FIG. 1 shows the NIR spectrum of a standard.

An example of the formation and representation of this initial spectral database is described by means of FIGS. 1 and 2.

FIG. 1 shows the NIR spectrum of a standard in which one can display as the spectral quantity the absorbance measured as a function of the wave number. Similar spectra are thus likewise established in identical manner for each standard. In the present sample representation, nine standards have been analyzed. Based on these spectra, one draws up a table (spectral database A) a sample representation of which is shown in FIG. 2 for a limited number of wave numbers.

Thus, in the table of FIG. 2 (which thus corresponds to a truncated view—two parts of the table are shown with different selected wave numbers), one may notice in the left column the references allowing an identification of the nine standards and on the first line the value of the wave number or ranges of wave numbers; the content of the table thus indicates the values of the spectral quantities (in the present case, the absorbances) corresponding to the pair "standard reference/wave number". These spectral quantities can be every type of signal characterizing the spectra, such as the absorbances, transmittances, reflectances, etc.; the absorbances or optical densities being the signals most commonly used. As an example, we shall also term as signals the derivatives of the absorbances or any other measurement resulting from another type of mathematical treatment of said absorbances.

The limited number of available standards is generally dictated by the client and/or the end user, who desire to utilize responsive and reliable methods of inspection while limiting the need to have a large quantity of standards beforehand and having to perform an analysis by the conventional methods.

One characteristic of the method according to the present invention is that it thus allows one to overcome the need, dictated by the prior art, to have a very large number of standards. For example, the present invention allows one to characterize a sample product based on a number of available standards less than 100, or even less than 60, or less than 50. It has even been possible to obtain very convincing results with the help of the present invention based on fewer than 40 available standards, or even fewer than 30 or even 20. A minimum of 10 available standards is preferred, however, even though the present invention has already been used with success with a minimum of 5 available standards.

For the present invention, the following description and the claims, it is obvious to the skilled person that the spectra can be realized as a function of wavelengths (and/or ranges of wavelengths), since the wave number is represented by the inverse of the wave length.

For the present invention, the following description and the claims, the standards shall also be called "germs" ["G"], the two terms being interchangeable.

A second optional step, and preferred according to the present invention, then consists in eliminating "polluting" wavelengths and wavelength ranges from the spectral database A. This step involves 1. repeating at least twice, preferably at least three times, more preferably at least five times, the same spectral analysis as the one done during the first step, and this on at least one of the available standards, preferably on at least two or even on all of said standards;
2. constructing a spectral database B from the measurements done under point 1 above;
3. calculating for each standard selected under point 1 above and for each wavelength and/or wavelength range (of the spectral database A) the standard deviations (σ) of the measurements recorded in database B;
4. identifying in database B the wavelengths and/or wavelength range for which the standard deviation is greater than a predetermined value;
5. eliminating from spectral database A the measurements corresponding to the wavelengths identified under point 4 above.

Thus, according to one preferred mode of execution of the present invention, the use of the second step above allows one to obtain an improved spectral database A'; an example of an improved spectral database A' is shown in FIG. 4.

An example representing the spectral database B is illustrated in FIG. 3 by a table.

One can see here that the same spectral analysis was repeated ten (10) times on the same sample and that the corresponding values of spectral quantities have been listed in the table. The last three rows of the table correspond respectively and consecutively to the mean spectral quantity value VGSmoyenne ("VGSm") which corresponds to the sum of the spectral quantity values divided by the number ("n") of analyses performed (VGSm=[Σ VGS]/n), where n=10 in the present representation;

the standard deviation ("σ") which corresponds to the difference between VGSmax and VGSmin in each column of the table;

the ratio (σ/(VGSm/100)) whose value (in percent) is calculated by dividing the standard deviation by the mean value of the spectral quantity, and multiplying the result by one hundred.

Thus, the last row of the table lets one identify in the database B the wavelengths and/or wavelength ranges for which the ratio (σ/(VGSm/100)) is greater than a predetermined value. According to one mode of execution of the present invention, one identifies in table B the columns (the wavelengths and/or wavelength ranges) for which the value of the ratios (σ/(VGSm/100)) is greater than 2% (preferably greater than 1.5% or even 1%); next, one eliminates from database A said columns, namely, the values of spectral quantities corresponding to the "polluting" wavelengths. The corresponding columns (that is, those whose wavelength and/or wavelength range are identical) will then be eliminated from spectral database A. It should be noted that in the above examples tables A and B are representations not having any true relation with each other; it should also be noted that tables A and B have been truncated in order to give a visual representation; in reality, these tables comprise a multitude of columns representing the wavelengths and/or wavelength ranges extracted from the corresponding spectrum, as explained further below in the description.

Thus, one example of the improved spectral database A' is illustrated in FIG. 4.

An essential characteristic of the method according to the present invention consists in that the establishing of the improved spectral database A' does not need at this stage to make reference [to] and/or [have] the slightest correlation with the chemical and/or physico-chemical properties of the standards. In fact, this second step is totally independent.

A third consecutive step of the method according to the present invention consists in the actual enlargement of the spectral database A (or the improved spectral database A'). This step consists in generating synthetic standards (also known as "intergerms" ["IG"] from the available standards and from their values of spectral quantities. For example, to generate these IGs one can produce combinations of several available standards of the first step above and populate the spectral database A (or the improved spectral database A') by means of these combinations. These combinations can be made in random fashion or in an oriented fashion as described further on in the text. Said combinations can consist in any kind of mathematical treatment applied to the values of spectral quantities of the standards G. According to one preferred mode of execution of the present invention, said combination consists in a barycenter of the values of spectral quantities ("VGS") of at least two standards. For example, one could produce these combinations among two, three, or a greater number of available standards at the start, preferably among all the available standards at the start.

An example of a corresponding formula for the generating of a synthetic standard (IG) from the standards G (to which the VGS correspond) is $$[\Sigma Ri \times VGSi]/[\Sigma Ri]$$

where i is a whole number from 1 to the number of standards G chosen for this combination and R is a real number such that $$[\Sigma Ri] > 0, \text{ and}$$

$$|[\Sigma R^*i]|/[\Sigma Ri] < 0.3, \text{ preferably } < 0.15,$$

And with R* representing only the negative real numbers. This latter formula can also be described as being the absolute value of the sum of the negative real numbers divided by the sum of all the real numbers.

According to a preferred mode of execution of the present invention, at least one of the Ri is a negative real number (R*).

Proceeding in this way, it is thus possible to enlarge the spectral database A (or the improved spectral database A') by means of synthetic standards (also known as "intergerms" or "IG") and thus obtain an enlarged spectral database E.

According to one preferred mode of execution of the present invention, when the number of standards of the spectral database A (or A') is "N", the number of intergerms IG is at least greater than 1.5 N, preferably greater than 2 N, most preferably greater than 5 N, or even greater than 10 N.

On sample representation of the enlarged spectral database E is illustrated in FIG. 5 by a table. One can see here that synthetic standards (or intergerms "IG") have been generated by mathematical combinations and that the values of corresponding spectral quantities have been recorded in the table E. As an example, one can observe in table E (FIG. 5):

six intergerms "IG" (I2G022, I2G011, I2G036, I3G038, I3G025 and I3G019;

in columns 3 to 5, the germs used to generate each of said intergerms;

in column 2, the weighting applied to the germs selected for the calculation of the VGS of the intergerms (for example, for the calculation of the intergerm I2G036, a weighting of (0.44 times the germ A0000008+0.56 times the germ A0000004) has been applied).

An essential characteristic of the method according to the present invention consists in that the establishment of the enlarged spectral database E has no need at this stage to make reference to and/or the slightest correlation with the chemical and/or physico-chemical properties of the standards. In fact, this enlargement step is totally independent.

A fourth additional optional and preferred step according to the present invention then consists in a supplemental enlargement of the spectral database A or the enlarged spectral database E by means of another type of synthetic standard which we shall call "extragerms" ("EG"). This step is particularly relevant when the target product being analyzed contains a plurality of chemical compounds.

It consists of registering in a first sequence the spectral data of at least one spectrum corresponding to one (or more) of the chemical compounds of the target product (also known as "Poles"). Next, in a second sequence, one proceeds with an additional enlargement of the spectral database by using said Pole(s) and combining them with the germs "G" (thus, one produces a combination of their values of spectral quantity, VGS).

This second sequence consists in generating synthetic standards (also known as "extragerms" ["EG"]) from the Pole(s) and the available standards and their values of spectral quantities. For example, to generate these EGs one can make combinations of Pole(s) and of several available standards of the first step above and populate the spectral database A and/or E by means of these combinations. These combinations can be made in random fashion or in an oriented fashion as described further on in the text. Said combinations can consist in any kind of mathematical treatment applied to the values of spectral quantities of the standards G and of the Pole(s). According to one preferred mode of execution of the present invention, said combination consists in a barycenter of the values of spectral quantities ("VGS") of the selected standards G and/or the Pole(s). For example, one could produce these combinations among at least one Pole and one, two, three, or a greater number of available standards at the start, preferably with all the Poles corresponding to all the chemical compounds making up the target product.

An example of a corresponding formula for the generating of a synthetic standard of type EG from Pole(s) and standards G (to which the VGS correspond) is $$[\Sigma Ri \times VGSi + \Sigma Rj \times VGSj]/[\Sigma Ri + \Sigma Rj]$$

where i is a whole number from 1 to the number of standards G chosen for this combination, j is a whole number from 1 to the number of Pole(s) chosen for this combination and R is a real number such that $$[\Sigma Ri + \Sigma Rj] > 0, \text{ and}$$

$$|[\Sigma R^*i]|/[\Sigma Ri + \Sigma Rj] < 0.3, \text{ preferably } < 0.15, \quad (I)$$

with R* representing only negative real numbers, and preferably each Rj should be such that the ratio Rj/[ΣRi+ΣRj] is always between the opposite number of the minimum content and the maximum content by weight percentage of the Poles j in the target product.

The above formula (I) can also be stated as being the absolute value of the sum of the negative real numbers "i" divided by the sum of all the real numbers. According to one preferred mode of execution of the present invention, at least one of the Ri is a negative real number (R*).

Proceeding in this way, it is thus possible to enlarge the spectral database A and/or E by means of synthetic standards ("EG") and thus obtain an enlarged spectral database EE. Optionally, said Poles and their VGS can also be integrated in the spectral database EE but this does not constitute a preferred mode of execution according to the present invention.

According to one preferred mode of execution according to the present invention, when the number of standards of the spectral database A (or A') is "N" and the number of "Poles" is "M", the number of extragerms "EG" is at least greater than N×M, preferably greater than 1.5 N×M, preferably greater than 2 N×M.

According to one mode of execution of the present invention, the number of poles is less than 15, for example less than 10.

According to one mode of execution of the present invention, the number of poles is less than 0.2 times the number of standards, for example, less than 0.1 times the number of standards.

A sample representation of the enlarged spectral database EE is illustrated in FIG. 6 by the table EE. One can see here that the "Poles" as well as the generation of the synthetic standards "EG" (extragerms) by mathematical combinations and the values of the corresponding spectral quantities have been recorded in the table.

As an example, one can observe in the table EE (FIG. 6):

six extragerms "EG" (MEG001 to MEG006);

in column 2 ("Pole"), the reference of the poles used (for example, the Pole PAL054 is a particular type of alkylate used in the composition of gasolines constituting the standards of the database);

in column 3, the reference of the germ used to generate each of said extragerms;

in column 4, the weighting applied to the Poles (X)—the weighting applied to the germs being thus (1-X). For example, to calculate the extragerm MEG001, a weighting of (0.15 times the Pole PAL054+0.85 times the germ A0000009 has been applied).

An essential characteristic of the method according to the present invention consists in that the establishment of the enlarged spectral database EE has no need at this stage to make reference to and/or the slightest correlation with the chemical and/or physico-chemical properties of the standards. In fact, this enlargement step is totally independent.

A fifth additional optional and preferred step according to the present invention likewise consists in a supplemental enlargement of the enlarged spectral database E and/or EE by means of another type of synthetic standard which we shall call "extragerms'" ("EG'"). This step is again particularly relevant when the target product being analyzed contains a plurality of chemical compounds.

It consists of registering in a first sequence the spectral data of at least one spectrum corresponding to one (or more) of the chemical compounds of the target product (also known as "Poles").

Next, in a second sequence, one proceeds with an additional enlargement of the spectral database E or EE by using said Pole(s) and combining them with the intergerms "IG" (combination of their VGS).

This second sequence consists in generating synthetic standards (also known as "extragerms'" ["EG'"]) from the Pole(s) and the "intergerm" standards ("IG") (and optionally germs "G") and their values of spectral quantities. For example, to generate these EG's one can make combinations of Pole(s) and of several intergerms "IG" from the third step above (and optionally germs G from the first step) and populate the spectral database E and/or EE by means of these combinations.

These combinations can be made in random fashion or in an oriented fashion as described further on in the text. Said combinations can consist in any kind of mathematical treatment applied to the values of spectral quantities of the synthetic standards (intergerms) "IG" and of the Pole(s) (and optionally the germs "G").

According to one preferred mode of execution of the present invention, said combination consists in a barycenter of the values of spectral quantities ("VGS") of the intergerms IG and/or the Pole(s) (and optionally the germs "G"). For example, one could produce these combinations among at least one Pole and one, two, three, or a greater number of the "IGs" of the third step, preferably with all the "IGs"; and optionally with at least one of the germs "G", preferably with all of the germs "G". These combinations will preferably be made with all the available Poles corresponding to all the chemical compounds making up the target product.

An example of a corresponding formula for the generating of a synthetic standard of type EG' from Pole(s) and synthetic standards IG (to which the VGS correspond) is $$[\Sigma Ri \times VGSi + \Sigma Rj \times VGSj + \Sigma Rk \times VGSk]/[\Sigma Ri + \Sigma Rj + \Sigma Rk]$$

where k is a whole number between 1 and the number of synthetic standards IG chosen for this combination, i is a whole number from 0 (preferably 1) to the number of standards G chosen for this combination, j is a whole number from 1 to the number of Pole(s) chosen for this combination, and R is a real number such that $$[\Sigma Ri + \Sigma Rj + \Sigma Rk] > 0, \text{ and}$$

$$|[\Sigma R^*i] + [\Sigma R^*k]|/[\Sigma Ri + \Sigma Rj + \Sigma Rk] < 0.3, \text{ preferably} < 0.15, \quad (II)$$

with Rk being preferably always positive,
with R* representing only the negative real numbers,
AND preferably each Rj should be such that the ratio Rj/[ΣRi+ΣRj+ΣRk] is always between the opposite number of the minimum content and the maximum content in weight percent of the Poles j in the target product.

Formula (II) above can also be stated as being the absolute value of the sum of the negative real numbers "i" divided by the sum of all the real numbers. According to one preferred mode of execution of the present invention, at least one of the Ri is a negative real number (R*).

Proceeding in this way, it is thus possible to enlarge the spectral database E and/or EE by means of synthetic standards ("EU") and thus obtain an enlarged spectral database EEI. Optionally, said Poles and their VGS can also be integrated in the spectral database E but this does not constitute a preferred mode of execution according to the present invention.

According to one preferred mode of execution of the present invention, when the number of synthetic standards IG of the spectral database E is "Z" and the number of "Poles" is "M", the number of extragerms' "EG'" is at least greater than Z×M, preferably greater than 1.5 Z×M, preferably greater than 2 Z×M.

According to another preferred mode of execution of the present invention, when the number of synthetic standards IG of the spectral database E is "Z", the number of germs G is N and the number of "Poles" is "M", the number of extragerms "EG'" is at least greater than Z×M, preferably greater than 1.5 Z×M, preferably greater than 2 Z×M.

According to one mode of execution of the present invention, the number of poles is less than 15, for example less than 10.

According to one mode of execution of the present invention, the number of poles is less than 0.2 times the number of standards, for example, less than 0.1 times the number A sample representation of the enlarged spectral database EEI is illustrated in FIG. 7 by the table. One can see here the "Poles" as well as the generation of the synthetic standards "EG'" (extragerms') by mathematical combinations and that the values of the corresponding spectral quantities have been recorded in the table.

As an example, one can observe in the table EEI (FIG. 7):
  six extragerms' "EG'" (MEP001 to MEP006);
  in column 5 ("Pole"), the reference of the poles used (for example, Pole PAL037 is a particular type of alkylate used in the composition of gasolines making up the standards of the database);
  in columns 2 to 4, the reference of the intergerms (combinations of germs) used to generate each of said extragerms;
  in column 6, the weighting applied. For example, to calculate the extragerm MEP004 there has been applied a weighting of [0.9 times an intergerm (corresponding to 0.306 times the germ A00000061–0.0530 times the germ A0000009+0.647 times the germ A0000002)+0.1 times the pole PAL037].

An essential characteristic of the method according to the present invention consists in that the establishment of the enlarged spectral database EEI has no need at this stage to make reference to and/or the slightest correlation with the chemical and/or physico-chemical properties of the standards. In fact, this enlargement step is totally independent. The present invention thus concerns a method of generation and optimization of a spectral database able to be used in a process of characterization of a target product by topological spectral analysis based on a limited number of available standards, method consisting, in a first step,
  of performing the same spectral analysis on said standards, and
  forming from the spectra obtained a spectral database A of several wavelengths and/or wavelength ranges,
characterized in a second optional step in that one eliminates from spectral database A the "polluting" wavelengths and/or wavelength ranges from spectral database A, involving
  1. repeating at least twice, preferably at least three times, more preferably at least five times, the same spectral analysis as the one done during the first step, and this on at least one of the available standards, preferably on at least two or even on all of said standards;
  2. constructing a spectral database B from the measurements done under point 1 above;
  3. calculating for each standard selected under point 1 above and for each wavelength and/or wavelength range (of the spectral database A) the standard deviations (a) of the measurements recorded in database B;
  4. identifying in database B the wavelengths and/or wavelength range for which the standard deviation is greater than a predetermined value; and
  5. eliminating from spectral database A the measurements corresponding to the wavelengths identified under point 4 above and thus obtaining an improved spectral database A', and also characterized by a third consecutive step which consists in the enlargement of the spectral database A (or the improved spectral database A'), involving making combinations of several standards of the first step and populating the spectral database A (or the improved spectral database A') by means of these combinations (known as synthetic standards or intergerms "IG") and thus obtaining an enlarged spectral database E, and also characterized by a fourth optional consecutive step which consists in the enlargement of the spectral database E, involving a first sequence of adding to the enlarged spectral database E at least one spectrum corresponding to at least one (or more) of the chemical compounds of the target product (also known as "Poles") and in a second sequence making mathematical combinations of said Pole(s) with at least one standard G of the first step and/or at least one of the standards IG of the third step and populating the spectral database E by means of these combinations (known respectively as synthetic extragerm standards or "EG" or synthetic extragerm' standards "EG'") and thus obtaining an enlarged spectral database EE (or EEI).

After having formed the enlarged spectral database according to the methodology developed above, it is possible to use any kind of conventional mathematical analysis to characterize a sample based on the enlarged spectral database.

According to one preferred mode of execution of the present invention, prior to this characterization an additional intermediate step consists in then defining an effective method of discrimination able to reveal homogeneous subgroups of products which preferably obey the same types of spectrum/property relationships thanks to a strong analogy of molecular structure.

The methods of discrimination can be based exclusively on techniques of mathematical analysis (such as factorial analysis and/or analysis by principal components). Although some of these mathematical methods may prove useful, the present invention preferably uses at least one other empirical step to accomplish this type of discrimination, an empirical step based on a visual spectral analysis of the aforementioned standards and/or poles; even though this does not constitute a preferred mode of execution according to the present invention, this visual analysis could also be done on the reconstituted spectra (based on their calculated VGS) of the intergerms and/or extragerms. This empirical step thus makes it possible to reveal minuscule differences between the spectra in question, differences which after verification may turn out to be synonymous with the existence of homogeneous subgroups of products, even if one believed at the outset that the totality of the population of products was homogeneous. This technique of discrimination thus makes it possible to reveal differences among the products even when the end user was still unaware of such.

As a reminder, one essential characteristic of the method of establishing the aforementioned enlarged spectral database according to the invention is that it does not have to make reference to and/or have the least correlation with the chemical and/or physico-chemical properties of the standards. According to one preferred mode of execution of the present invention, the same is true of the discrimination step described here.

Thus, according to one mode of execution of the present invention, the discrimination step then consists in defining, from the enlarged spectral database, aggregates (preferably at least two aggregates), spaces of n dimensions representing the combinations of said aggregates (preferably planes—or two-dimensional spaces—representing pairs of aggregates), and corresponding spectral boxes.

According to one mode of execution of the present invention, the method of discrimination also involves at least two particular preferred characteristics:
1. the fact that said method involves an iteration phase during which one verifies the efficacy of the spectral box and thus the relevance of the selected aggregates; and
2. the fact that the aggregates are built up from at least one visual analysis of the appearance of the spectra, then allowing one to construct the equations of the aggregates as a function of the values of spectral quantities VGS.

The aggregates are thus defined as mathematical functions of the values of spectral quantities of the enlarged spectral database making it possible to regroup and/or discriminate and/or separate families of products within the enlarged spectral database. These aggregates can thus be represented in general by the function Agg=f (VGSi).

According to one preferred mode of execution of the present invention, said function obeys equations of type $$\frac{\sum_{k=1}^{n}\sum_{i=1}^{p} aiWi^{\alpha}Wk^{\beta}}{\sum_{i=1}^{q} aiWi^{\alpha}}$$

or preferably of type $$\frac{\sum_{i=1}^{p} aiWi^{\alpha}}{\sum_{i=1}^{q} aiWi^{\alpha}}$$

in which
W represents the values of discriminant spectral quantities VGS,
a are positive real numbers,
p and q represent the selection of the VGS at the wavelengths and/or wavelength ranges relevant to the discrimination step, and
$\alpha$ and $\beta$ are exponents between 1/3 and 3.

As for the iteration phase during which one verifies the efficacy of the spectral box and thus the relevance of the aggregates selected, it is enough to add columns to the previously determined spectral database representing the equations of the discriminant aggregates, calculate the value of said aggregates for each of the standards and/or intergerms and/or extragerms and/or poles of the spectral database, produce the graphical representations (preferably in spaces of two dimensions for each pair of aggregates), and thus visualize whether the discrimination has resulting in revealing homogeneous subgroups of products. This discrimination step thus makes it possible to divide the spectral database into several (at least two) distinct families (homogeneous subgroups of products), preferably at least three distinct families.

As an example, FIGS. 8 and 9 represent respectively
a graph whose abscissa/ordinate axes correspond to two discriminant aggregates, and a table of corresponding values, whose columns show several discriminant aggregates of which the first two were used to produce the graph (FIG. 8).

These figures clearly explain how one succeeds in revealing several homogeneous subgroups of products.

Thus, the present invention also concerns a method of characterization of a product by topological spectral analysis.

The characterization of a product according to the present invention may involve a determination and/or a prediction of any chemical, physical or physico-chemical property of said product.

According to one mode of execution of the present invention, the first step is thus characterized by the formation of a spectral database, preferably an enlarged spectral database as described in the present specification.

As already indicated above, the graphic representations of the databases (tables) in the appended figures are truncated views, since in reality said databases constitute a multitude of columns representing the wavelengths and/or wavelength ranges (or, equivalently, the wave numbers or wave number range) extracted from the corresponding spectra.

According to one mode of execution of the present invention, the number of wavelengths chosen can be from 2 to 1000, for example, from 5 to 200 or from 40 to 80.

The wavelengths chosen can be at regular intervals such as 1 to 50 nm or every 10 to 50 nm or every 15 to 35 nm or every 1 to 5 nm or any other nanometers; or they can be at irregular intervals, such as intervals of 1 to 200 nm, for example 1 to 100 or 1 to 50 in particular from 2 to 50 or 4 to 50 or 10 to 60 nm, which can be chosen randomly according to a variation of the shape of the spectral curve at this wavelength, for example, a peak, a valley or a shoulder, or chosen with chemical or statistical criteria such as factorial analysis. The wavelengths can be in the region of 600 to 20,000 nm, for example from 625 to 2600 nm, for example from 800 to 2600 nm, in particular from 1500 to 2600 or from 2000 to 2550 nm. The wave numbers can be in the region from 16,600 to 500, for example from 16,000 to 3840 cm-1, for example from 12,500 to 3840 cm-1 in particular from 6660 to 3840 or from 5000 to 3900 cm-1; the corresponding frequencies in Hertz can be obtained by multiplying these wavelengths by $3 \times 10(exp)10$ cm/s.

Before being able to determine and/or predict a property of a sample, one must of course measure the values of that property for the standards and, optionally, for the poles. Thus, according to one mode of execution of the present invention the chemical, physical and/or physico-chemical properties of the standards (and optionally of the poles) are determined by means of conventional analysis techniques. As an example of conventional analysis techniques but not limited to this, one can mention gas-phase chromatography for chemical compositions. Even though it goes without saying that the standards are chosen to cover the range in which the method is supposed to be used, in one preferred mode of execution the present invention allows working with a limited number of standards thanks to the aforementioned methodology of enlargement of the spectral database.

Thus, in the present invention, one adds to the spectral database the measured values of the desired properties for said standards (and optionally the poles); once the spectral database has been enlarged, one then calculates the values of said properties for the synthetic intergerm (and optionally extragerm) standards based on the formulas which were used to generate these synthetic standards; this calculation is done simply by replacing the values of spectral quantities VGS with the measured values of said properties of the standards (and optionally the poles) used in the formulas (and optionally, for the extragerms, by the values already calculated for the intergerms). One thus ends up with a spectral database formed from a number of points (standards and optionally intergerms, poles and extragerms) with which the desired properties (measured and calculated) are associated. A sample embodiment (truncated view) is shown in FIG. 10.

As an illustration, this is an enlarged spectral database E composed of standards (A) and intergerms (IG). The table has been supplemented with characteristics of the sought target products, namely, the values RON and MON (the research octane number (RON) and the motor octane number (MON)). These characteristics were thus measured for the standards and calculated for the intergerms.

In the specification of EP0742900, one then compares the signals, for example, the absorptions (or their derivatives) for the unknown sample with signals, for example the absorptions (or their derivatives) at the same wavelength of the standards, and selects the standards having the smallest differences. Next, one takes the mean of the properties of these selected standards in order to determine the property of the unknown sample. One thus reconstitutes a calculated spectrum of the target product to which the characteristic (property) thus calculated corresponds.

According to one preferred mode of execution of the present invention, this signal comparison is thus not performed on the entire spectral database but only on a representative portion of the spectral database for the homogeneous subgroup to which the sample belongs. This part of the spectral database is defined by making preferable use of the aforementioned discrimination method (discriminant aggregates).

Next, one compares the signals, for example the absorptions (or their derivatives or any other value of a spectral quantity) for the unknown sample (target product) with the same signals and at the same wavelength of the standards and/or intergerms and/or extragerms and/or poles belonging to the same homogeneous subgroup, and one selects in the spectral database the standards and/or intergerms and/or extragerms and/or poles having the smallest differences.

Whatever the method used, we shall call hereinafter the points close to the target product the "close neighbor" points. Next, for example, one can take the mean of the properties of these standards and/or intergerms and/or extragerms and/or poles selected to determine the sought characteristic (property) of the unknown sample.

According to one particular mode of execution of the present invention, the close neighbors chosen are those having the smallest mean values for the absolute difference at each wavelength i between the value of the spectral quantity (represented, for example, by the absorbance or a derivative of the latter) Wix for the target product (sample/unknown product) and the corresponding signal Wim for the close neighbor. The means may refer for example to the mean value of Wix−Wim (regardless of its sign, i.e., an absolute difference), or of (Wix−Wim)exp2. For each close neighbor in the spectral database for the type of product in question, one finds the mean difference as described and selects the close neighbor having the smallest mean differences, namely, at least 1 but preferably 2, up to 1000 of the smallest ones, for example, 2 to 100 or 2 to 20 but in particular 2 to 10 and especially 2 to 6 of the smallest ones. This selection of the closest neighbors can be done by any known method, such as one can advantageously use the methods described in the specification of patent EP0742900 (for example, by determining the index of proximity).

According to one particular mode of execution of the present invention, the number of close neighbors can be equal to 1, preferably greater than or equal to 2, even more preferably greater than or equal to 3.

According to one mode of execution of the present invention, the number of close neighbors is equal to or less than 50, for example, equal to or less than 20, or even 10.

As indicated above, once the "close neighbor" points have been selected, one can easily take the mean of the properties of these selected close neighbors (standards and/or intergerms and/or extragerms and/or poles) to determine the property of the unknown sample (the target product). Thus, one reconstitutes a calculated spectrum of the target product to which the characteristic (property) thus calculated corresponds.

However, and this constitutes a preferred mode of execution of the present invention, the applicant has discovered unexpectedly a significant improvement of the precision and robustness of its method during the determination of the sought characteristic (for example, a property) of a target product by taking a weighted average of the properties of these "close neighbor" points (whatever the standards and/or intergerms and/or extragerms and/or poles), said weighting being a linear or nonlinear function inversely proportional to the distance between the sample ("the target product") and the "close neighbor" points selected, this weighting being represented for example by the formula $$\text{WEIGHT} = \frac{\frac{1}{di^\alpha}}{\sum_1^n \frac{1}{di^\alpha}}$$

where α is a positive number preferably between 0.5 and 1.5,
di is the distance between the target product and the close neighbor i, and
n is the total number of close neighbors.

Thus, one will apply a weighting of this type to the properties measured (and optionally calculated) of the "close neighbors" to obtain the property of the target product.

One thus reconstitutes a calculated spectrum of the target product to which the characteristic (property) thus calculated corresponds.

In other words, the calculation of the characteristic Z of the target product is done thanks to the corresponding characteristics Zi of the close neighbor points, assigning to the characteristics of said close neighbor points a weight which is larger in said calculation as they are closer to the target product.

Thus, the present invention also concerns a method of characterization of a target product involving the following steps:
1. Formation of a spectral database comprising samples, their spectra and their measured characteristics ("CAR", such as the property "P"),
2. Spectral analysis of the target product and comparison of the spectrum obtained (Spectre PC) with the spectral data of the database,
3. Identification of "close neighbor" points of the target product, and
4. Calculation by topology of the characteristic of the target product (CARpc/top, for example the property Ppc/top) as a function of the corresponding characteristics of the close neighbor points, characterized in that the calculation of step 4 is based on a weighting associated with the inverse of the distance between the target product and the close neighbor points.

One can use the method of the invention to determine more than one property P at a time, for example, at least 2, in particular between 1 and 30, for example 2 to 10 properties at a time. Of course, one can use different numbers of standards chosen for each property.

According to another preferred mode of execution of the present invention, the applicant has discovered another particularly effective alternative method.

This method consists in combining one of the aforementioned topological methods of characterization of the target product with any other mathematical model different from the topological methods (preferably a regression model) and enabling a characterization of the target product based on the values of spectral quantities VGS (for the same property).

Thus, this method involves the preliminary formation of a mathematical model able to calculation the properties of the products as a function of the values of spectral quantity (VGS) of the database, preferably a regression model (for product characterization based on the previously established spectral database); this spectral database can be either the aforementioned database A or preferably the database E, EE or EEI, or a selection of said databases. Preferably, this database will be the same as the one used for the topological method.

This alternative method for characterization of a target product involves the following steps:
1. Formation of a spectral database comprising samples, their spectra and their measured characteristics ("CAR", such as the property "P"),
2. Spectral analysis of the target product and comparison of the spectrum obtained (Spectre PC) with the spectral data of the database,
3. Identification of "close neighbor" points of the target product, and
4. Calculation by topology
   4.1. of the characteristic of the target product (CARpc/top, for example the property Ppc/top), and
   4.2. of its spectrum so calculated (spectre PCcalc),
5. Formation from the spectral database of a mathematical model able to calculate the characteristic of a product based on the spectral database (CAR/mod, for example property P/mod),
6. Calculation of the characterization of the target product PC by the following formula $$CARpc = CARpc/\text{top} + [CARpc/\text{mod} - CARpc\text{calc}/\text{mod}]$$

where
CARpc is the calculated value of the characteristic of the target product sought,
CARpc/top is the value calculated by topology (close neighbor points) of the characteristic of the target product,
CARpc/mod is the value calculated by the mathematical method of the characteristic of the target product, and
CARpccalc/mod is the value calculated by the mathematical method of the characteristic of the target product calculated (by means of the spectral data obtained in point 4.2).

The characterization of a product according to the present invention can thus consist in a determination and/or a prediction of any chemical, physical or physico-chemical characteristic of said product and/or the identification of a type and/or family of products.

For example, one can determine the presence of individual chemical compounds within a composition as well as their concentrations; one can also determine every kind of property, certain of which are exemplified below.

Thus, one can use the method for the physico-chemical determination or the prediction regarding at least one feedstock or a product used in an industrial oil refining process and/or in petrochemical operations or obtained with the help of the latter. The process can be a hydrocarbon conversion or a separation process, preferably a process of reforming or catalytic cracking or hydrotreatment or distillation or blending. In particular, one can use it to determine at least one property of a feedstock and/or the prediction and/or the determination of at least one property and/or a yield of a product coming from a certain number of different processes such as processes for separating petroleum products such as atmospheric distillation, vacuum distillation or separation by distillation, under pressure greater than atmospheric pressure, as well as thermal or catalytic conversion, with or without partial or total hydrogenation, of a petroleum product, such as catalytic cracking, for example fluid catalytic cracking (FCC), hydrocracking, reforming, isomerization, selective hydrogenation, viscoreduction or alkylation.

The use of the method in blending operations involving the production and/or the determination of at least one property of a blend of liquid hydrocarbons (optionally with other additives such as alkyl ethers) is of particular value, whether or not this method involves the determination of a blend index for the property in question for each constituent of the blend. In this method as applied to the blend, one can obtain the blend indices simply by calculation and without having to prepare physical blends of standards other than those contained in the database. One can combine in linear or nonlinear fashion the blend indices in the stability ranges in order to determine from the value of this combination a value for at least one property of the obtained blend. One can produce the blend by mixing at least two components from among butane, steam-cracked hydrogenated gasoline, isomerate, reformate, MTBE or TAME, and gasoline derived by FCC. One can repeat this process by adding numerically the other constituents separately to the basic hydrocarbon liquid to determine a series of blend indices and then determine from these indices the properties of the multiconstituent blend.

Examples of properties which can be determined and/or predicted are the following: for automotive fuels/gasolines, at least one among the research octane number (RON), the motor octane number (MON) and/or their arithmetic mean, with or without lead additive and/or content of methyl-t-butyl ether or methylisoamyl ether and/or benzene.

For automotive fuels/gasolines, at least one of the vapor tension, the density, the volatility, the distillation curve, such as the percentage distilled at 70° C. and/or at 100° C., the oxygen content or the benzene or sulfur content, the chemical composition and/or the gum content, for example expressed in mg/100 ml and/or the lead sensitivity (one determines these properties in particular to use in the blending operations).

For Diesel fuels or gas oil, at least one of the cetane index (for example, measurement at the engine), the calculated cetane index, the cloud point, the "discharge point", the filter ability, the distillation curve, the density for example at 15° C., the flash point, the viscosity for example at 40° C., the chemical composition, the sensitivity to additives and the percentage of sulfur.

For the distillation products coming from crude petroleum, for example under atmospheric pressure, at least one of the density, the sulfur percentage, the viscosity at 100° C., the distillation curve, the paraffin content, the residual carbon content or the Conradson carbon content, the naphtha content, the flash point of oil, the cloud point for gas oil, such as light gas oil, and/or the viscosity at 100° C. and/or the sulfur content for atmospheric residues and the yield for at least one of the cuts, gasoline (Bp. 38 to 95° C.), benzene (Bp. 95 to 149° C.), naphtha (Bp. 149 to 175 C), kerosene (Bp. 175 to 232° C.), light gas oil (Bp. 232 to 342° C.), heavy gas oil (Bp. 342 to 369° C.) and that of the atmospheric residue above 369° C.

For at least one of a feedstock or a product of a catalytic cracking process, such as a FCC process, at least one of the density, the sulfur percentage, the aniline point, the gas oil index, the gasoline index, the viscosity at 100° C., the index of refraction at 20° C. and/or at 60° C., the molecular mass, the distillation temperature, for example the distillation temperature at 50%, the aromatic carbon percentage, the total nitrogen content and the factors characterizing the cracking capacity of the feedstock, such as the KUOP, the crackability factor, the cokability factor, and the yield, for example, of gas, of gasoline, of gas oil or of residue. Thus, one can determine the yields and/or the properties of different products obtained by the distillation of cracked products such as RON and/or MON, without anti-knock additive or lead for the gasoline cut and the viscosity at 100° C. for the distillation residue.

For at least one of a product or a feedstock of a process of catalytic reforming, at least one of the density, the distillation temperature and/or the chemical composition (expressed in percent) of straight-chain saturated hydrocarbons, isoparaffins, naphthenes, aromatic substances and olefins.

For at least one of a product or a feedstock of a gasoline hydrogenation process, at least one of the density, the distillation temperature, RON and/or MON, the vapor tension of gasoline without anti-knock or leaded additive, the volatility, the chemical composition (expressed in percentage), of straight-chain saturated hydrocarbons, isoparaffins, naphthenes, aromatic substances such as benzene and the mono/di-substituted benzenes, olefins such as cyclical and noncyclical olefins, diolefins, and the maleic anhydride index.

The invention claimed is:

1. Method of generation and optimization of a spectral database able to be used in a process of characterization of a target product by topological spectral analysis based on a limited number of available standards, the method comprising the following steps:
   (a) performing the same spectral analysis on said available standards, and
      forming from the spectra obtained a spectral database A of several wavelengths and/or wavelength ranges,
   (b) if required, eliminating from spectral database A polluting wavelengths and/or wavelength ranges from spectral database A, involving the following steps:
      (1). repeating at least twice the same spectral analysis as done during the step (a), and on at least one of the available standards;
      (2). constructing a spectral database B from measurements done under point 1 above;
      (3). calculating for each standard selected under point 1 above and for each wavelength and/or wavelength range of the spectral database A the standard deviations ($\sigma$) of the measurements recorded in database B;
(4). identifying in database B the wavelengths and/or wavelength range for which the standard deviation is greater than a predetermined value; and
(5). eliminating from spectral database A the measurements corresponding to the wavelengths identified under point 4 above to develop an improved spectral database A', and
(c) enlarging either the spectral database A or the improved spectral database A', by making combinations of several standards of step (a) and populating either the spectral database A or the improved spectral database A' by means of the generated combinations to develop an enlarged spectral database E for use in determining characterization of a target product.

2. Method according to claim 1 further including a step consisting in the enlargement of the spectral database E, involving a first sequence of adding to the enlarged spectral database E at least one spectrum corresponding to at least one chemical compound of the target product and in a second sequence making mathematical combinations of said target product with at least one standard G of the step (a) and/or at least one of the generated combinations of the step (c) and populating the spectral database E by means of these combinations to develop an enlarged spectral database EE.

3. Method according to claim 1 wherein generation of a synthetic standard from standards G to which values of spectral quantity correspond is done by means of the formula $$[\Sigma Ri \times VGSi]/[\Sigma Ri]$$

where i is a whole number from 1 to the number of standards G chosen for this combination and R is a real number such that $$[\Sigma Ri] > 0, \text{ and}$$

$$|[\Sigma R*i]|/[\Sigma Ri] < 0.3, \text{ preferably } < 0.15,$$

with R* representing only the negative real numbers; and preferably at least one of the Ri is a negative real number (R*).

4. Method according to claim 2 wherein generation of a synthetic standard EG from the standards G to which the values of spectral quantity correspond and at least one Pole is done by means of the formula $$[\Sigma Ri \times VGSi + \Sigma Rj \times VGSj]/[\Sigma Ri + \Sigma Rj]$$

where i is a whole number from 1 to the number of standards G chosen for this combination, j is a whole number from 1 to the number of Pole(s) chosen for this combination
and R is a real number such that $$[\Sigma Ri + \Sigma Rj] > 0, \text{ and}$$

$$|[\Sigma R*i]|/[\Sigma Ri + \Sigma Rj] < 0.3, \text{ preferably } < 0.15, \quad (I)$$

with R* representing only negative real numbers, and each Rj should be such that the ratio Rj/[$\Sigma Ri + \Sigma Rj$] is always between an opposite number of a minimum content and a maximum content by weight percentage of the Poles j in the target product; and at least one of the Ri is a negative real number (R*).

5. Method according to claim 2 wherein generation of a synthetic standard from synthetic standards IG, at least one Pole, and optionally from the standards G is done by means of the formula $$[\Sigma Ri \times VGSi + \Sigma Rj \times VGSj + \Sigma Rk \times VGSk]/[\Sigma Ri + \Sigma Rj + \Sigma Rk]$$

where k is a whole number between 1 and the number of synthetic standards IG chosen for this combination, i is a whole number from 0 to the number of standards G chosen for this combination, j is a whole number from 1 to the number of Pole(s) chosen for this combination, and R is a real number such that $$[\Sigma Ri + \Sigma Rj + \Sigma Rk] > 0, \text{ and}$$

$$|[\Sigma R*i] + [\Sigma R*k]|/[\Sigma Ri + \Sigma Rj + \Sigma Rk] < 0.3, \text{ preferably } < 0.15, \quad (II)$$

with Rk being preferably always positive,
with R* representing only the negative real numbers,
and preferably each Rj should be such that the ratio Rj/[$\Sigma Ri + \Sigma Rj + \Sigma Rk$] is always between the opposite number of a minimum content and a maximum content in weight percent of the Poles j in the target product; and preferably at least one of the Ri is a negative real number R*.

6. Method according to claim 1 wherein the spectral analysis is of near infrared type.

7. Method according to claim 1 wherein the spectral data is selected from the group consisting of: the absorbances, transmittances, reflectances or optical densities.

8. Method according to claim 1 wherein the number of available standards to make the database A is less than 100.

9. Method according to claim 8 wherein the number of available standards to make up the database A is less than 40 available standards.

10. Method according to claim 2 wherein the number of target products is less than 0.2 times the number of standards.

11. Method according to claim 1 wherein the step (b) is done by eliminating from the database the polluting wavelengths, namely, the spectral data at wavelengths for which the value of the ratios ($\sigma$/(VGSm/100)) is greater than 2%.

12. The method according to claim 1, wherein use of characterization of the target product involves the following steps:
(1). formation of a spectral database comprising samples, their spectra and their measured characteristics,
(2). spectral analysis of the target product and comparison of the spectrum obtained with the spectral data of the database,
(3). identification of "close neighbor" points of the target product, and
(4). calculation by topology of the characteristic of the target product as a function of the corresponding characteristics of the close neighbor points,
characterized in that the calculation of step 4 is based on a weighting associated with an inverse of a distance between the target product and the close neighbor points.

13. The method according to claim 1, wherein use of characterization of the target product involves the following steps:
(1). formation of a spectral database comprising samples, their spectra and their measured characteristics,
(2). spectral analysis of the target product and comparison of the spectrum obtained with the spectral data of the database,
(3). identification of "close neighbor" points of the target product, and (4). calculation by topology
   (4.1). of the characteristic of the target product, and
   (4.2). of its spectrum so calculated,
(5). formation from the spectral database of a mathematical model able to calculate the characteristic of a product based on the spectral database,
(6). calculation of the characterization of the target product PG by the following formula $$CARpc = CARpc/\text{top} + [CARpc/\text{mod} - CARpc\text{calc}/\text{mod}]$$

where
   CARpc is the calculated value of the characteristic of the target product sought,
   CARpc/top is the value calculated by topology (close neighbor points) of the characteristic of the target product,
   CARpc/mod is the value calculated by the mathematical method of the characteristic of the target product, and
   CARpccalc/mod is the value calculated by the mathematical method of the characteristic of the target product calculated (by means of the spectral data obtained in point 4.2).

14. Method of generation and optimization of a spectral database to be used in a process of characterization of a target product by topological spectral analysis based on a limited number of available standards, the method comprising of the following steps:
   (a) performing the same spectral analysis on the available standards, and forming from the spectra obtained a spectral database A of several wavelengths and/or wavelength ranges;
   (b) if required, eliminating from spectral database A polluting wavelengths and/or wavelength ranges, said elimination comprising the following steps:
      (1) repeating at least twice the same spectral analysis as done during step (a) and on at least one of the available standards;
      (2) constructing a spectral database B from measurements done under step (1) above;
      (3) calculating for each standard selected under step (1) above and for each wavelength and/or wavelength range of the spectral database A standard deviations ($\sigma$) of the measurements recorded in database B;
      (4) identifying in database B the wavelengths and/or wavelength range for which the standard deviation is greater than a predetermined value; and
      (5) eliminating from spectral database A the measurements corresponding to the wavelengths identified under step (4) above to develop an improved spectral database A'
   (c) enlarging either the spectral database A or the improved spectral database A' by making combinations of several standards of step ($\sigma$) and populating either the spectral database A or the improved spectral database A' by means of the generated combinations to develop an enlarged spectral database E for use in determining characterization of a target product; and
   (d) enlarging spectral database E, involving a first sequence of adding to the enlarged spectral database E at least one spectrum corresponding to at least one chemical compound of the target product, and in a second sequence making mathematical combinations of the target product with at least one standard G of step (a) and/or at least one of the generated combinations of step (c) and populating the spectral database E by means of these combinations to develop an enlarged spectral database EE for use in determining characterization of a target product; and
   (e) generation of a synthetic standard from the at least one standard G to which values of spectral quantity correspond is done by means of the formula $[\Sigma Ri \times VGSi]/[\Sigma Ri]$ where i is a whole number from 1 to the number of standards G chosen for this combination and R is a real number such that $[\Sigma Ri] > 0$, and $|[\Sigma R^*i]|/[\Sigma Ri] < 0.3$, preferably $<0.15$, with R* representing only the negative real numbers; and at least one of the Ri is a negative real number R*.

* * * * *